United States Patent [19]
Davison

[11] Patent Number: 5,652,963
[45] Date of Patent: Aug. 5, 1997

[54] CAMOUFLAGE AND PROTECTIVE HEADGEAR

[76] Inventor: George M. Davison, 65 W. Chapel Ridge, Pittsburgh, Pa. 15238

[21] Appl. No.: 532,930

[22] Filed: Oct. 2, 1995

[51] Int. Cl.$^6$ .................... A61F 9/02; A61F 9/04
[52] U.S. Cl. .................. 2/206; 2/9; 2/244; 2/426; 2/900
[58] Field of Search .................. 2/410, 6.6, 422, 2/424, 15, 10, 11, 426, 431, 438, 445, 452, 9, 171, 173, 181.4, 206, 207, 209.11, 209.13, 900, 244; 428/919

[56] References Cited

U.S. PATENT DOCUMENTS

| | | | |
|---|---|---|---|
| D. 274,385 | 6/1984 | Newcomb | D2/234 |
| D. 317,063 | 5/1991 | Johnson | D29/17 |
| 3,015,104 | 1/1962 | Crosson et al. | 2/900 |
| 3,832,418 | 8/1974 | Piper | 2/206 |
| 4,106,124 | 8/1978 | Green | 2/900 |
| 4,250,577 | 2/1981 | Smith | 2/427 |
| 4,285,068 | 8/1981 | Ross | 2/202 |
| 4,781,959 | 11/1988 | Gottlieb | 428/95 |
| 4,812,031 | 3/1989 | Evans | 351/46 |
| 5,091,996 | 3/1992 | Kirby | 2/206 |
| 5,146,622 | 9/1992 | Blutstein | 2/900 |
| 5,148,550 | 9/1992 | Hodgkinson et al. | 2/424 |
| 5,247,706 | 9/1993 | Mark | 2/9 |

Primary Examiner—Michael A. Neas
Attorney, Agent, or Firm—Charles A. Bevelacqua

[57] ABSTRACT

A camouflage and protective headgear which may be worn by a human. The headgear comprises an upper fabric portion which will encircle a portion of the head and forehead of a person wearing it. The top edge of the upper fabric portion falls along a line lying at approximately the hairline of the wearer and the bottom edge falls along a line lying at approximately the eyebrows of such a person. The upper fabric portion has an upwardly extending fringe along at least a portion of the top edge thereof. The upper fabric portion may also have a downwardly extending fringe along at least a portion of the bottom edge thereof. Preferably the headgear has a lower fabric portion encircling a portion of the nose and face of the person wearing it and having a top edge which falls along a line lying approximately at the bottom of the eyes of such person and a bottom edge which falls along a line lying at approximately at the bottom of the jaws and chin of such person. The lower fabric portion has a downwardly extending fringe along at least a portion of the bottom edge. The lower fabric portion may also have an upwardly extending fringe along at least a portion of its top edge. Goggles or a substantially rigid nose piece are provided to maintain a separation between the upper and lower fabric portions so that a person wearing the headgear can see through the separation. A headgear is shown which includes a cushioning and absorbent liner to absorb perspiration from areas under the headgear and to cushion the head of a person wearing it from rigid portions of the headgear.

13 Claims, 3 Drawing Sheets

U.S. Patent    Aug. 5, 1997    Sheet 1 of 3    5,652,963
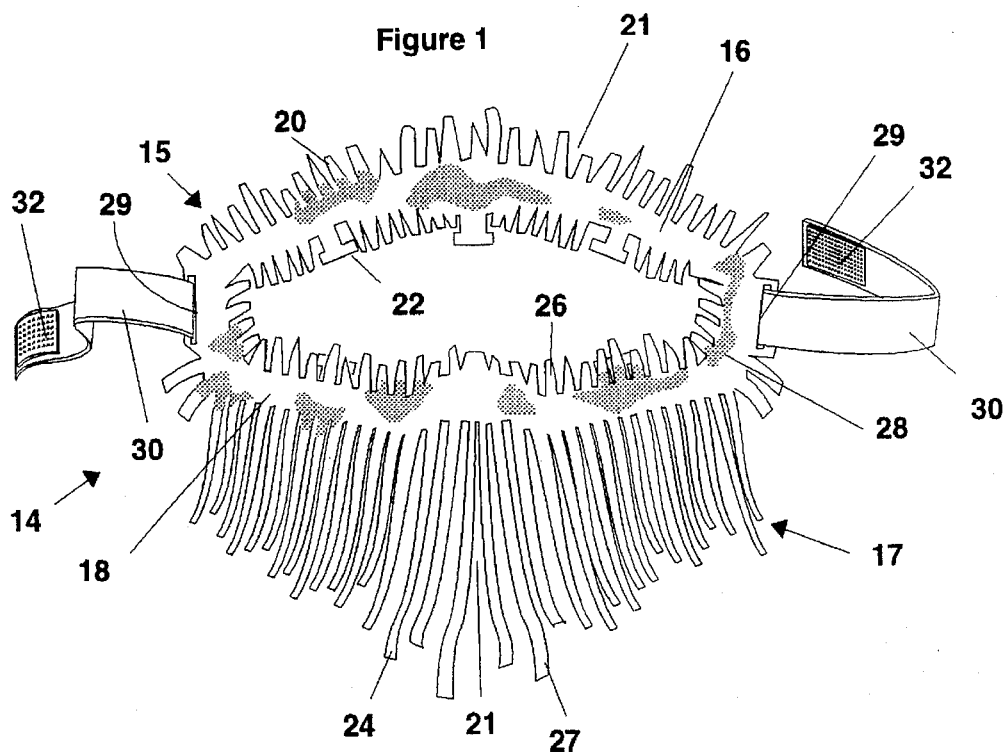
Figure 1
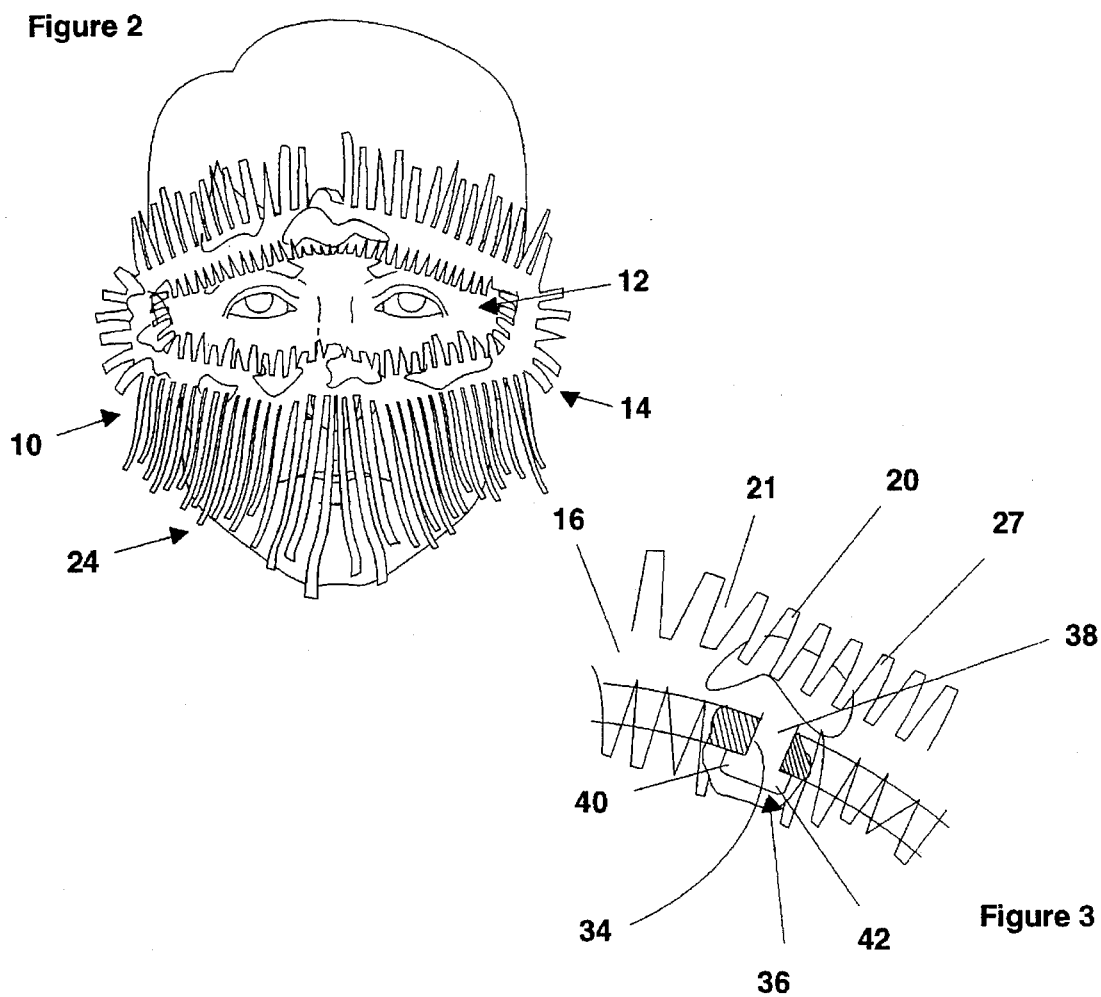
Figure 2
Figure 3

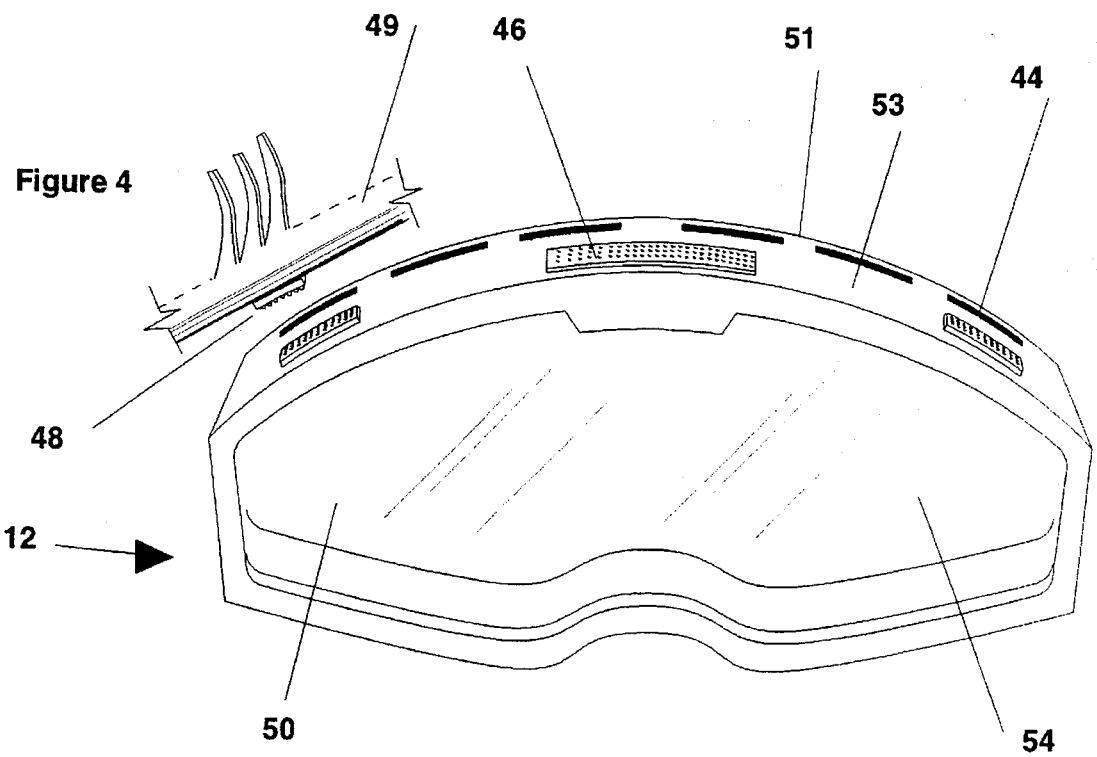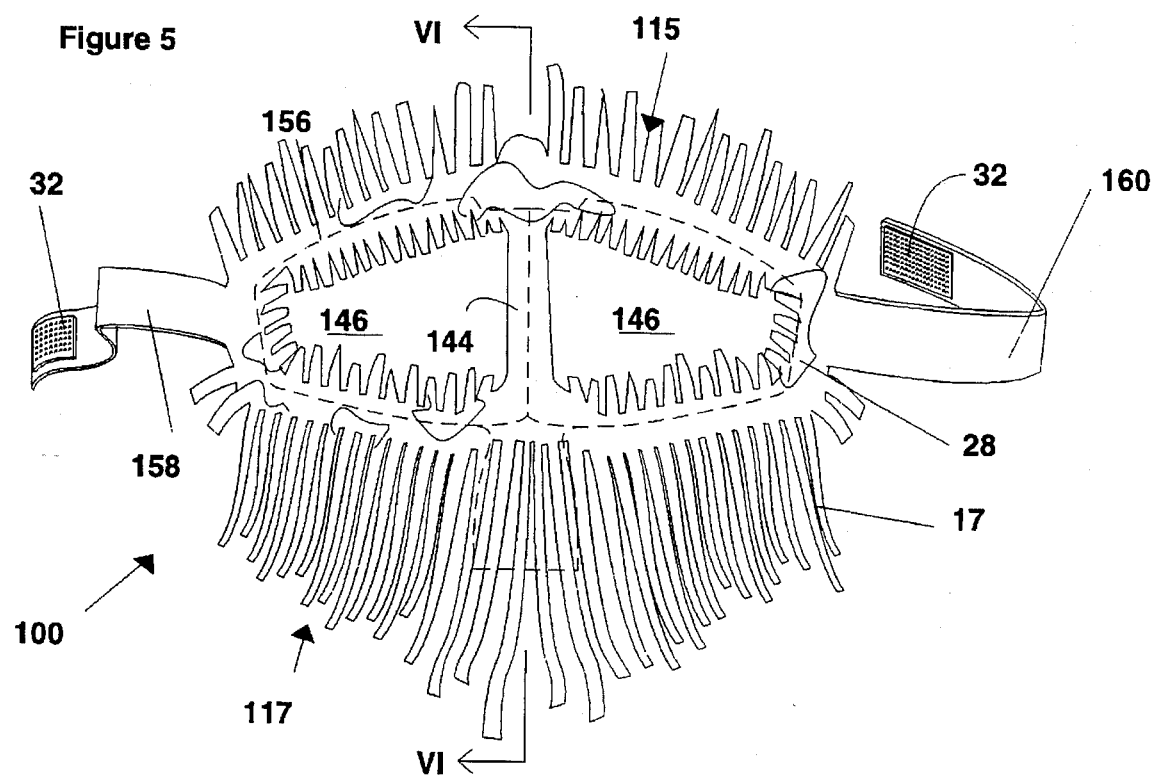

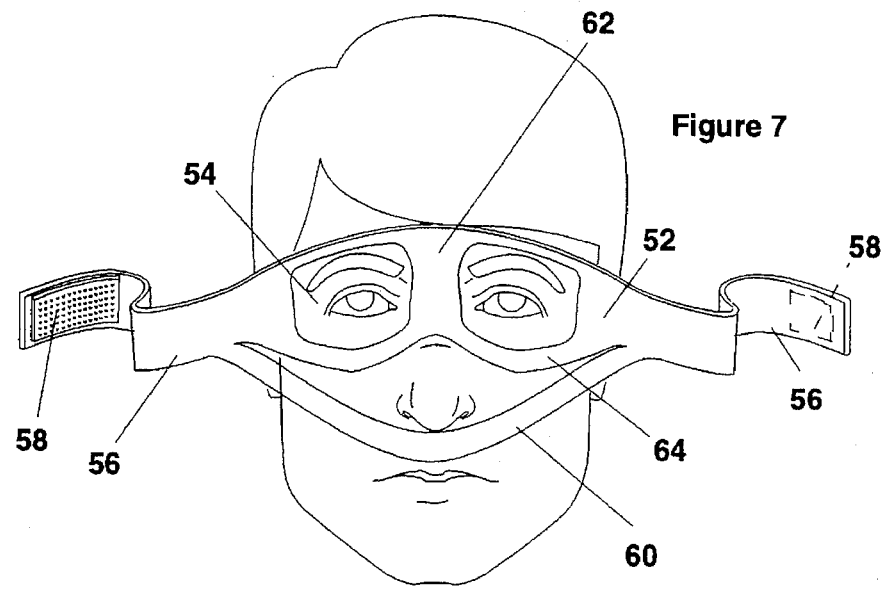
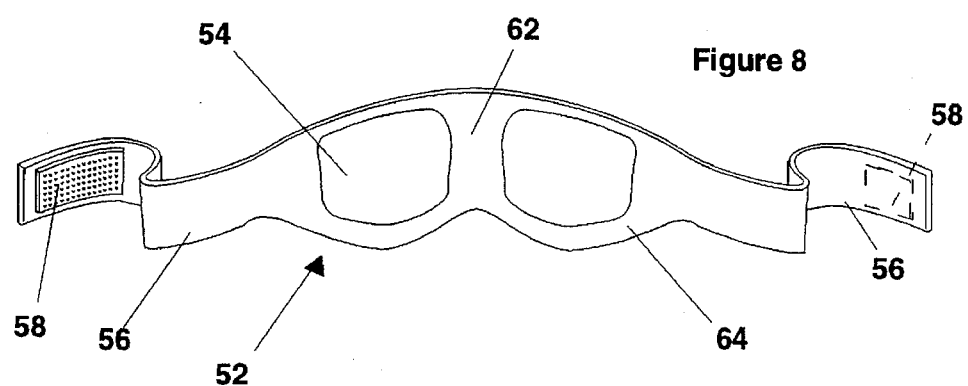
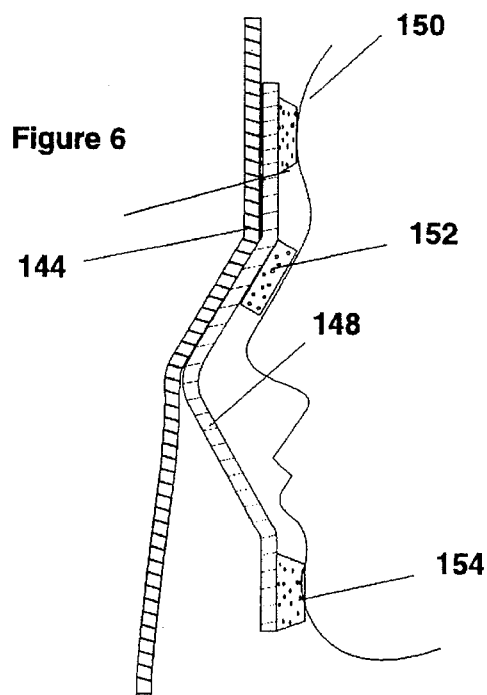

CAMOUFLAGE AND PROTECTIVE HEADGEAR

FIELD OF THE INVENTION

This invention relates to camouflage and protective headgear for military, quasi-military or simulated military activities and the like and particularly for use in the sports activity commonly known as "paint ball tag game" or "paint ball war game".

BACKGROUND OF THE INVENTION

In military, quasi-military, such as certain police actions and simulated military, such as the paint ball tag game, activities it is desirable that the participants wear clothing which will protect them against certain types of projectiles and debris and to make them less visible to others. It is known that it is more difficult to ascertain the presence of an object against a background such as woods or a cultivated or uncultivated field if the object has an irregular and/or broken outline and is covered with an irregular or random color pattern in certain earth tones or colors sometimes found in the environment where the activities for which this invention is intended often take place. This is the reason for the familiar camouflage color pattern used on military clothing and equipment. In the paint ball sport it is also desirable to protect the participants from the paint ball projectiles which the players shoot at one another to produce a paint mark that indicates that the player has been hit and thus disabled or eliminated from the game and to raise the comfort level of the participants by providing a cushion in areas of potential pressure from the headgear and by absorbing perspiration from areas of the head.

Although protective body clothing for camouflage and protective effect is relatively common for use in the paint ball game activity, a suitable and effective headgear such as is disclosed by the present invention has not previously been available. Previously available protective face and headgear has consisted of close fitting masks of solid plastic construction which were hot and sweat inducing and which restricted breathing or impaired the ability of the wearer to move his or her head or has consisted of a hood made of cloth fabric tied around the neck and very awkward to wear and complicated to put on and secure. Such available headgear has not found wide acceptance by participants in the paint ball game.

Examples of the rigid mask type of headgear are shown in design U.S. Pat. No. 317,063 to Johnson, U.S. Pat. Nos. 4,250,577 to Smith and 5,148,550 to Hodgkinson et al. The mask in the Johnson patent would cover the face, eyes, nose and mouth of the wearer, would be hot and uncomfortable to wear and would make it very difficult to breath or speak. This is also true of the Smith and Hodgkinson et al. masks. Smith attempts to overcome a portion of the problem by providing a "venturi nose covering on the mask to draw exhaled air from behind the mask permitting a fresh air flow behind the mask while moving." The problem of fresh air flow and cooling while the wearer is stationary is not solved by this construction. It should be noted that in the activities for which the invention is intended the wearer may be stationary for much of the time. Hodgkinson et al.'s approach is to provide slits in the mask as air vents and to flare the lower end of the mask which would be near the wearer's throat so that the wearer can lower his head without the lower end of the face portion of the mask making contact with the wearer's throat.

U.S. Pat. No. 5,247,706 to Mark shows a face shield which can be worn with eyeglasses. Mark is not concerned with camouflage and uses a substantially transparent piece of plastic as the shield which is itself easily visible by virtue of glare and reflection and through which the face and eyes of the wearer are easily detected. Mark does not address the problems of ventilation and reduction of moisture from perspiration and from exhaled breath.

U.S. Pat. No. 5,091,996 to Kirby shows a cloth hood worn over the head and extending to the shoulders. Kirby is concerned with camouflage and with avoiding the undulating movement of the loose lower portion of the hood which would be readily discernible to others from whom the wearer is trying to remain concealed. Kirby uses a smooth, woven fabric and employs a wire frame which is intended to fit closely and tightly against the contour of the face of the wearer and limit motion of the portion of the hood hanging downward from the eye area of the wearer. This would make the hood annoying and uncomfortable to wear for more than Short periods of time and make it unsuitable for the purpose for which the invention is intended.

The U.S. Pat. No. 4,812,031 to Evans shows a pair of eyeglasses which have a piece of open-weave netting or mesh fabric mounted over each of the lenses. This serves to at least partially camouflage the eyes of the wearer. In addition a camouflage pattern is printed on the fabric to further hinder observation of the eyes of the wearer.

What is needed and is provided by the present invention is protective and camouflage headgear which does not interfere with the activity of the wearer or with his or her breathing or vision but which provides a high level of protection, reduces visibility of the head, neck, face and eye covering of the wearer, reduces the effect of moisture from breathing and perspiration, is easily put on and removed and incorporates goggles or some other form of eye protection or can be associated with or attached to preexisting goggles or other eye protection to reduce visibility of such eye protection and provides cushioning in areas where pressure from the headgear may occur on the face and head of the person wearing it.

The fabric portion of the headgear should be constructed for easy separation from the goggles so that the fabric can be washed or otherwise cleaned after use. The headgear should have an irregular outline and be provided with a camouflage pattern of suitable colors to make it difficult to detect in the environment in which it is expected to be used.

SUMMARY OF THE INVENTION

According to the present invention there is provided a protective and camouflage headgear which is worn with a goggle portion which protects the eyes of the wearer. The goggle portion may be a part of the headgear provided by the invention or may be one of several currently available types of goggles. In either case, the portion surrounding the goggles is constructed from a relatively thick sheet of plastic or other non-woven fabric or the like and cooperates with the goggles to protect and cover the forehead, face and neck. The fabric is slit, cut and colored to provide an irregular color pattern and an irregular fringe-like surface and outline to reduce its visibility and the visibility of the goggles or other eye protection especially in wooded, grassy or low light environment while providing a substantial degree of protection to the wearer from mechanical injury by a paint ball or similar projectile and from staining of the wearer's hair, forehead and neck by the paint from a splattering paint ball. In addition the headgear may be provided with an absorbent liner which helps reduce the discomfort from perspiration and moisture in the wearer's breath and also acts as a cushion to protect the head and face of the wearer from pressure from the typical hard frame of the goggles.

If the headgear is to be worn with existing available eye protection or goggles it is provided with elastic securing means or means complementary to those which may be provided on the eye protection device. For example, some goggles may be provided with slits or holes or bails to receive some form of strap or similar securing means. In such case the fabric portion of the headgear may be provided with complementary structures which cooperate with those on the goggles to facilitate attachment of the fabric to the goggles and removal therefrom. On the other hand if the goggles are included as a part of the headgear of the invention, then almost any available form of securing means which is suitable for the purpose may be utilized. For example, elastic bands may be provided or the fabric may be provided with buttons or disc-like formations and the adjacent portions of the goggles may have slits or button holes formed in them to receive the buttons or discs. Hook and loop fabric or snap-buttons or holes and pegs are a few other examples of structures which may also be used to provide the attachment means. The absorbent liner may be independently supported on the head of the wearer by separate attaching means such as elastic band or other adjustable means or alternatively may be sewn or otherwise adhered to the surface of the goggles which will lie adjacent to the head and face of the wearer.

It would also be possible to construct the headgear by securing straps or strands of fabric directly to the frame of goggles with an adhesive or any of various other known means for attaching the strips of fabric to the frame of the goggles.

While the invention has been described primarily in connection with its application and use in connection with the paint ball tag game or paint ball war game, it is not restricted to such use and could find application in hunting, military and police maneuvers and many other activities.

OBJECTS AND ADVANTAGES OF THE INVENTION

It is one of the objects of this invention to provide a protective headgear suitable for wear by a human which headgear does not interfere with vision or movement of the wearer's head.

Another object of the invention is to provide such protective headgear which is relatively light weight and streamlined in appearance but which provides substantial mechanical protection to the face, head and neck of the wearer.

Another object of this invention is to provide protective headgear which includes a relatively soft absorbent liner which helps prevent accumulation of moisture from perspiration and exhaled breath of the wearer so the headgear is more comfortable to wear and cushions the head and face of the wearer from pressure of the headgear.

Still another object of the invention is to provide such protective headgear which incorporates protection for the eyes of the wearer without unduly interfering with or restricting the vision of the wearer.

It is also an object of the invention to provide protective headgear which helps to camouflage the face, head and neck portions from observation by others in the vicinity.

A further object of the invention is to provide protective headgear which is compatible with and can be worn in association with presently available goggles or other eye protective devices.

Another object of this invention is to provide protective headgear of the type described which will help to reduce visibility of such goggles or other eye protective devices to others in the vicinity.

Yet another object of the invention is to provide protective headgear which can be easily cleaned as by washing without damage or deterioration.

It is an object of the invention to provide protective headgear which is strong, durable and effective but which is light in weight, pliable and unobtrusive so that it is not burdensome or tiring to wear.

It is another object of this invention to provide such headgear constructed so as to camouflage the wearer's head from observation by others.

Another object of this invention is to provide protective and camouflage headgear which does not restrict or impede the wearer's normal breathing.

Yet another object of this invention is to provide protective and camouflage headgear for military, quasi-military and simulated military activities which does not limit or interfere with the user's movement of the head or shoulders.

Still another object of this invention is to provide protective and camouflage headgear which includes goggles and which can be easily disassembled from the goggles for cleaning and can be cleaned without damage.

These and other objects and advantages of the invention will become more readily apparent to those persons skilled in the art from the following detailed description particularly when such description is taken in conjunction with the attached drawings and the appended claims.

BRIEF DESCRIPTION OF THE DRAWINGS

FIG. 1 is a plan view of the fabric portion of the invention.

FIG. 2 is a perspective view of a complete assembly of the invention as it would appear on the head of a person.

FIG. 3 shows the attachment between attaching means employed on one form of currently available goggles and the fabric portion of the invention.

FIG. 4 shows the construction of goggles which can be used as part of the headgear of this invention and illustrates one of the methods of attaching the fabric portion of the headgear to a goggle frame.

FIG. 5 illustrates an alternate form of the invention which can be worn without goggles.

FIG. 6 is a cross-sectional view taken along the line VI—VI in FIG. 5.

FIG. 7 is a perspective view of one form of absorbent liner in place on the head of a wearer before the remainder of the headgear is placed over it but with the support straps not secured to each other.

FIG. 8 is a perspective view of an alternative form of absorbent liner.

DESCRIPTION OF THE PREFERRED EMBODIMENTS

Referring now to the drawings in which, for the sake of clarity, like parts in the different views are referred to with like reference numbers, the camouflage and protective headgear of this invention is indicated in FIG. 2 by the number 10. The headgear comprises a goggle portion 12 and an outer fabric portion 14 which is shown separately in FIG. 1. The outer fabric portion of the invention is preferably made of non-woven material such as polyethylene foam or neoprene sheet material cut to a length sufficient to wrap the face and forehead of the wearer approximately from behind one ear to behind the other ear. Other non-woven materials, synthetic foams, leather, or a woven fabric may be employed. This outer fabric portion is comprised of an upper fabric portion generally designated 15 and a lower fabric portion generally designated 17. Upper fabric portion 15 has a solid upper central portion 16 and lower fabric portion 17 has a solid lower central portion 18. Above and below the solid upper central portion and the solid lower central portion the fabric is slit in a direction transverse to the length of the fabric to form fringes extending upwardly and downwardly from each of the solid central portions. The fringe extending upwardly from upper central portion 16 is designated by the number 20 and the fringe extending downwardly from upper central portion 16 is identified by the number 22.

The fringe extending downwardly from lower central portion 18 is designated by the number 24 while the fringe extending upwardly therefrom is identified by the number 26. As can be seen fringes 22 and 26 help to camouflage goggles or other eye protection.

Alternatively, downwardly extending fringe 22 or upwardly extending fringe 26 or both may be eliminated. The individual strands 27 of each of the fringes preferably are cut to randomly differing lengths and preferably may have printed or otherwise applied thereon low visibility colors or a camouflage design 28 or both to further reduce visual perception of the headgear in field conditions. Fringes 22 and 26 when utilized are made relatively short so that they will reduce visibility of the smooth continuous edge of the goggles but will not appreciably impair the vision of the wearer. The individual strands of upwardly extending fringe 20 are cut relatively coarsely or the fabric used for upper portion 15 may be of greater thickness than the fabric used for lower portion 17 or these strands may be made with both of these features so that fringe 20 will have sufficient rigidity to stand in a generally vertical direction and effectively cover and obscure the top of the head and hair of a person wearing the headgear.

It should be noted that the fringes 20, 22, 24 and 26 serve one or more of a variety of functions and may have a variety of specific embodiments. The fringes function in one respect to provide camouflage, in another to at least partially protect the face and hair of the wearer from being splashed with paint from a paint ball or other debris; and also to provide varying degrees of mechanical protection from projectiles, such as the paint balls, or from branches or palm fronds or leaves of other vegetation. To perform these functions the fringes must have a relatively substantial body to be able to mechanically deflect debris and projectiles, have a substantially continuous surface to protect against paint but must have a broken and irregular surface and outline to perform a camouflaging function.

The slits or cuts 21 used to create the fringe may be cut completely through the fringe fabric or may extend only partly through the fabric as long as it presents an uneven, discontinuous surface which is less noticeable than a continuous straight line. The cuts 21 may be made in a straight line, a curved line or may be made in intersecting angles. The normally downwardly extending fringes 22 and 24 may have relatively thin individual strands 27 while the upwardly extending fringes 20 and 26 may be more coarsely cut and the slits forming them may not be cut completely through the material of which they are made. Also as previously pointed out, the fabric from which the upwardly extending fringes are made, may be more rigid or thicker or both. As previously noted the fringes, especially those extending downward, may be made of individual strands directly secured to the goggle frame or similar structure.

Finally, the individual strands 27 of the fringes may be of random varying lengths and may be arcuate or angular in shape to help them perform their camouflage function. In addition, as previously stated, the fabric from which the headgear is made may be imprinted or otherwise have applied to it a less visible color or a camouflage design 28 before or after it is cut into the elements of the headgear.

The unfringed or solid portion of outer fabric portion 14 is provided with an opening 29, seen in FIG. 1, adjacent each of its ends to receive a strap 30 typically present on goggles, not shown in FIG. 1, with which the headgear may be worn. Strap 30 is customarily made of elastic material or also provided with an attached portion of hook and loop fastening material 32 or some other form of releasable fastener which is used to secure the goggles and the fabric portion 14 of the headgear to the head of the wearer. It should be understood that the headgear may be constructed with its own strap so that both the goggles and the headgear may be independently supported on the head of the wearer or only the headgear supplied with support straps whereby the goggles would be supported by attachment to the headgear. There is shown in FIG. 4 an example of goggles designated by the number 12 with which the headgear may be worn or which may constitute a part of the headgear. The goggles comprise lenses 50 surrounded for at least a portion of their perimeter by a substantially rigid frame 53. The inner edge 51 of the goggle frame which inner edge lies closest to the wearer's face and forehead is contoured to fit relatively closely to the adjacent portions of the face and forehead. The frames are provided with vent openings 44 which may be slots as shown or any other suitable opening. The goggle frame may also have secured thereto portions 46 of the hook or loop part of a hook and loop fastener or some other type of releasable fastener. A complementary part 48 of a hook and loop fastener or other fastener is secured to the fabric portion 14 of the headgear to permit its attachment to the goggles. A segment of the fabric portion of the headgear is shown in FIG. 4 and marked with the number 49. Thus the fabric portion of the headgear can easily be separated from the goggle portion to permit ready cleaning of both portions.

FIG. 7 shows the absorbent liner or inner fabric portion 52 as it would appear on the head of the wearer before the outer fabric portion 14 and any goggles or other eye protection are put on. The absorbent liner 52 is made from a soft, absorbent fabric material such as cotton or a similar natural or synthetic fabric or foam. It is constructed preferably in one piece in substantially the form of an eye and nose mask but in one form may also have an upper lip portion 60 which fits across the upper lip of the wearer under the nose. This inner fabric portion is provided with openings 54 which overlie the eyes of the wearer and permit unrestricted vision. Straps 56 are integrally formed with such mask or suitably attached thereto and extend from each side of the mask ending in an elastic portion or in some form of adjustable, detachable cooperating securing means 58 for attaching the liner to the head of a person. Alternately, the absorbent liner 52 may be sewed or otherwise adhered to the inner surface of the goggle frame which surface lies adjacent to the head and face of the wearer.

The liner 52 could also be made as part of the outer fabric portion or integrally attached thereto. However, it is preferred that it be provided as a separable element because in practice the liner may be changed several times during the course of a particular activity so that it can better absorb perspiration from the wearer who will be kept dryer and more comfortable. As can be seen the absorbent liner has several areas or portions 60, 62 and 64. Portion 60 lies across the upper lip of a person wearing the headgear, portion 62 lies across the forehead of such person and portion 64 fits across the upper cheeks and under the eyes. These areas correspond to the portions of a person's face and head where perspiration is most likely to occur and generally also correspond to areas contacted by the inner edge 51 of goggles 12. The absorbent liner absorbs much of this perspiration, making the wearer feel much more comfortable. The liner is made of material which is also relatively light and thin so that several liners can easily be carried in a pocket or with other articles in a small pouch or bag. When a liner becomes saturated it can quickly be removed and replaced with a dry one. As previously stated, the liner is relatively soft and also acts as a cushion against pressure from the frame 53 of goggles 12.

Referring now to FIG. 3, there is shown another form, in addition to a hook and loop fastener, of means for attaching the fabric portion 14 of the headgear to the goggle portion thereof. This means comprises a slot 34 in the frame of the goggles and a retainer tab 36 integral with the fabric portion of the headgear. Tab 36 has a neck portion 38, which has a width approximately equal to or slightly smaller than the width of slot 34, a toe part 40 and a heel part 42. The frame 53 of goggle portion 12 is substantially rigid while the fabric portion 14 is relatively soft and at least slightly deformable. This permits the fabric portion to be attached to the goggle portion as described below. The toe part 40, which is dimensioned to easily fit through slot 34, is inserted through slot 34, pressure is placed on tab 36 sufficient to slightly deform the parts of tab 36 so that the heel part 42 slips through slot 34 causing tab 36 to be releasably locked in slot 34. A sufficient number of tabs and slots are provided to suitably attach the fabric portion 14 to goggle portion 12.

It should be clearly understood that the upper and lower fabric portions of outer fabric portion 14 may both be made from one integral piece of fabric or may be made from separate pieces of fabric. Each of the fabric portions may have separate means for securing that respective fabric portion to goggles or other eye protection or to the head of a person wearing the headgear or only one of the fabric portions may be provided with means for securing the headgear to the head of a person and the other fabric portion provided with means for securing it to the one fabric portion which has means for securing the headgear to the head of a person.

In applications where it is not necessary or desirable to employ goggles the invention may be constructed without goggles as shown in FIG. 5. In this embodiment the headgear 100 includes upper and lower fabric portions 115 and 117 respectively similar to the upper and lower fabric portions of the embodiment previously described but also comprises a nose-piece 144 which joins the upper and lower fabric portions and keeps them separated from each other to leave openings 146 through which the wearer may see. To help retain the desired shape of the headgear in this embodiment the upper and lower fabric portions 115 and 117 as well as the nose-piece 144 or any one or more of them may be constructed of substantially thick and relatively rigid material or may be constructed of two or more layers of material to provide rigidity. Alternatively, as shown in FIG. 6 the nose-piece 144 may be reinforced with a backing 148 of strong rigid plastic such as polyethylene or dense polyethylene foam or any other suitable material. In the version of the invention shown in FIGS. 5 and 6, the headgear may be provided with relatively soft cushioning material, such as polyurethane foam, which would lie between the headgear and the forehead, nose and face of the wearer to make the headgear more comfortable to wear for long periods of time. As shown in FIG. 6 a strip 150 of cushioning material can be provided across the forehead, a strip 152 can be located down the nose-piece and a strip 154 can be located to contact the chin and/or jaw area. Such cushioning material or padding can be located substantially along the areas indicated by the dotted lines 156 in FIG. 5. The headgear of FIGS. 5 and 6 may be provided with straps 158 and 160 or similar means for attaching the headgear to the head of a person.

While I have shown and described specific embodiments of the invention, many variations and alternatives may be made to the specific arrangements and configurations shown without departing from the objects and scope of the invention as defined by the following claims.

I claim:

1. Camouflage and protective headgear which may be worn by a human, said headgear comprising:

an upper fabric portion having a top edge and a bottom edge and being constructed and arranged to encircle a portion of the forehead and head of a person wearing it, with said top edge falling along a line which would be approximately at the hairline of a person wearing it and said bottom edge falling along a line which would be approximately at the eyebrows of such a person, strap means attached to said upper fabric portion for securing the headgear on the head of a person wearing it, said strap means further being effective to maintain said headgear on the head of such person with the top and bottom edges of said upper fabric portion in the positions described with respect to the hairline and eyebrows of such person, and said upper fabric portion including an upwardly extending fringe extending along at least a part of the top edge of said upper fabric portion.

2. A camouflage and protective headgear as described in claim 1, further comprising:

a lower fabric portion joined to said upper fabric portion, and means extending between said upper fabric portion and said lower fabric portion and maintaining a separation between said upper and lower fabric portions at areas including portions of the areas which would be in front of the eyes of a person wearing the headgear whereby such a person could see through said separation.

3. A camouflage and protective headgear as set forth in claim 2 wherein at least one of said upper and lower fabric portions is made of a non-woven synthetic fabric.

4. A camouflage and protective headgear as set forth in claim 2 wherein said separation means includes a substantially rigid nose-piece occupying at least a part of the area which would overlie the nose of a person wearing the headgear.

5. A camouflage and protective headgear as set forth in claim 2 wherein said separation means includes goggles having a substantially rigid frame and occupying at least a part of the area which would overlie the eyes of a person wearing the headgear.

6. A camouflage and protective headgear as set forth in claim 2 wherein said upper and lower fabric portions each have a first end and a second end, said first ends are joined to each other and said second ends are joined to each other, said headgear further comprises a first strap portion extending from said first ends of said fabric portions and a second strap portion extending from said second ends of said fabric portions, and said first and second strap portions being provided with securing means at their free ends which cooperate with each other to removably secure said headgear to the head of a person.

7. A camouflage and protective headgear as set forth in claim 6 wherein all of said fabric portions and said first and second strap portions are integrally formed from a single piece of material.

8. Camouflage and protective headgear which may be worn by a human, said headgear comprising:

a lower fabric portion having a top edge and a bottom edge and being constructed and arranged to encircle a portion of the nose and face of a person wearing it, with said top edge falling along a line which would be approximately at the bottom of the eyes of a person wearing it and said bottom edge falling along a line which would be approximately at the jaws and chin of such a person, strap means attached to said lower fabric portion for securing the headgear on the head of a person wearing it, said strap means further being effective to maintain said headgear on the head of such person with the top and bottom edges of said lower fabric portion in the positions described with respect to the eyes and the jaws and chin of such person, and said lower fabric portion including a downwardly extending fringe extending along at least a part of the bottom edge of said lower fabric portion.

9. A camouflage and protective headgear as described in claim 8, further comprising:

an upper fabric portion joined to said lower fabric portion, and separation means extending between said upper and lower fabric portions and effective to maintain a separation between said upper and lower fabric portions at areas including portions of areas which will lie in front of the eyes of a person wearing the headgear whereby such a person could look through such separation.

10. A camouflage and protective headgear as set forth in claim 9 wherein the length of adjacent individual strands of said upwardly extending fringe are randomly made equal, longer or shorter so that the free end of said fringe forms a broken, non-uniform edge.

11. A camouflage and protective headgear as set forth in claim 9 wherein said separation means includes a substantially rigid nose-piece occupying at least a part of the area which would overlie the nose of a person wearing the headgear.

12. A camouflage and protective headgear as set forth in claim 9 wherein said separation means includes goggles having a substantially rigid frame and occupying at least a part of the area which would overlie the eyes of a person wearing the headgear.

13. A camouflage and protective headgear which may be worn by a human, said headgear comprising:

an upper fabric portion constructed and arranged to encircle a portion of the forehead and head of a person wearing it, a generally upwardly extending fringe forming the uppermost portion of said upper fabric portion, lower fabric portion constructed and arranged to encircle a portion of the face and jaw of a person wearing the headgear, a downwardly extending fringe forming the lowermost portion of said lower fabric portion, separation means extending between said upper and lower fabric portions, said separation means including goggles having a substantially rigid frame adapted to contact the face and forehead of a person wearing the headgear along a line defined by the contour of the frame of said goggles, a cushioning and absorbent liner constructed and arranged to be positioned between said rigid frame of said goggles and the face and forehead of a person wearing the headgear and covering an area which includes the line of contact between the frame of the goggles and the face and forehead of such person, and means for supporting said cushioning and absorbent liner on the head of such person.

* * * * *